(12) United States Patent
Shirazi (10) Patent No.: US 7,905,021 B2
(45) Date of Patent: Mar. 15, 2011

(54) INTERNATIONAL DINING KIT

(76) Inventor: Kamran Shirazi, San Francisco, CA (US)

( * ) Notice: Subject to any disclaimer, the term of this patent is extended or adjusted under 35 U.S.C. 154(b) by 283 days.

(21) Appl. No.: 11/607,322

(22) Filed: Dec. 1, 2006

(65) Prior Publication Data

US 2007/0101578 A1    May 10, 2007

Related U.S. Application Data (63) Continuation-in-part of application No. 11/200,666, filed on Aug. 10, 2005, now abandoned.

(51) Int. Cl.
*A47J 43/00* (2006.01)
(52) U.S. Cl. .............................. 30/147; 30/142
(58) Field of Classification Search ............ 30/147–150, 30/142, 143; D7/542–545; 7/112–113; 294/99.2; 220/574.1, 575, 762, 763
See application file for complete search history.

(56) References Cited

U.S. PATENT DOCUMENTS

| | | | |
|---|---|---|---|
| 33,730 A | 11/1861 | Ames | |
| 1,053,387 A | 2/1913 | Hawley | |
| 3,101,727 A | 8/1963 | Wiseman | |
| 3,136,416 A * | 6/1964 | Goldrosen | 206/372 |
| 3,586,161 A * | 6/1971 | Fong et al. | 206/372 |
| 3,637,248 A | 1/1972 | Arita | |
| 3,829,350 A * | 8/1974 | Davis | 428/134 |
| 4,576,408 A | 3/1986 | Maneki | |
| D284,442 S * | 7/1986 | Chan | D7/645 |
| 4,809,435 A | 3/1989 | Printz | |
| 4,930,637 A * | 6/1990 | DeRoseau | 206/541 |
| D310,465 S * | 9/1990 | Bonasia | D7/644 |
| D311,851 S | 11/1990 | Allardyce | |
| 4,995,154 A * | 2/1991 | Bamber | 30/147 |
| 5,056,173 A | 10/1991 | Brincat | |
| 5,327,650 A | 7/1994 | Rojas | |
| 5,431,465 A | 7/1995 | Shibata | |
| D362,160 S | 9/1995 | Brabeck et al. | |
| 5,791,053 A | 8/1998 | Koong | |
| 5,800,256 A | 9/1998 | Bermudez | |
| 6,067,717 A | 5/2000 | Perlman et al. | |
| D448,627 S | 10/2001 | Chan | |
| 6,328,360 B1 | 12/2001 | Freeman | |
| D463,220 S | 9/2002 | Yun | |
| 6,607,225 B1 | 8/2003 | Lai | |

(Continued)

FOREIGN PATENT DOCUMENTS

CN    1 623 476 A    6/2005

(Continued)

OTHER PUBLICATIONS

International West Coast Seafood Show 2006, Program of Exhibits and Events, Oct. 15-16, 2006, Los Angeles Convention Center, Los Angeles California, Diversified Business Communication.

*Primary Examiner* — Stephen Choi
(74) *Attorney, Agent, or Firm* — Kolisch Hartwell, P.C.

(57) ABSTRACT

The present disclosure teaches an international dining kit comprising a pair of multifunctional chopstick components. The components include a first chopstick component having a fork portion and a first chopstick portion; and a second chopstick component having a spoon portion and a second chopstick portion. The kit can also include additional functionality, such as a knife, a straw, and a dental cleaning component, as well as be disposable and/or biodegradable.

4 Claims, 3 Drawing Sheets

U.S. PATENT DOCUMENTS

| | | |
|---|---|---|
| 2002/0092181 A1 | 7/2002 | Choi |
| 2002/0096896 A1 | 7/2002 | Lai |
| 2003/0160467 A1 | 8/2003 | Lai |
| 2004/0051327 A1 | 3/2004 | Yoon |

FOREIGN PATENT DOCUMENTS

| | | |
|---|---|---|
| GB | 2 089 198 A | 6/1982 |
| GB | 2 350 778 A | 12/2000 |
| GB | 2 370 216 A | 6/2002 |
| JP | 4-215712 | 8/1992 |
| JP | 6090845 | 4/1994 |
| JP | 7213406 | 8/1995 |
| JP | 10-313998 | 12/1998 |
| JP | 10-337239 | 12/1998 |
| JP | 11-178689 | 7/1999 |
| JP | 11-216057 | 8/1999 |
| JP | 2000 135172 A | 5/2000 |
| JP | 2001 120415 A | 5/2001 |
| JP | 2001-157628 | 6/2001 |
| JP | 2001-258714 | 9/2001 |
| JP | 2002 238720 A | 8/2002 |
| JP | 2003-250684 | 9/2003 |
| JP | 2004261337 * | 9/2004 |

* cited by examiner

INTERNATIONAL DINING KIT

CROSS REFERENCE

This application is a continuation-in-part of U.S. patent application Ser. No. 11/200,666 filed Aug. 10, 2005 now abandoned, which is hereby incorporated herein by reference in its entirety.

BACKGROUND

1. Field of the Invention

This invention relates generally to an international dining kit comprising a pair of multifunctional chopstick components comprising a first chopstick component having a fork portion and a first chopstick portion; and, a second chopstick component having a spoon portion and a second chopstick portion.

2. Description of the State of the Art

It's common and accepted that people from different parts of the world will often prefer to eat using different styles of eating utensils, but unfortunately, they do not always have the utensils that they prefer readily available in all situations. The major items of cutlery in the western world, for example, are the knife, fork and spoon. Chopsticks, on the other hand, are the traditional eating utensils of East Asia, where China, Japan, Korea, and Vietnam are considered "chopstick countries," and Thailand is often now included in that list.

In East Asian cultures, children learn to use chopsticks as their first utensils. In China, for example, a child has usually gained the ability to eat every grain of rice in a ricebowl with chopsticks by the age of three. Moreover, in such cultures, the food is also more often prepared specifically for handling with chopsticks: the food generally contains small pieces, and the rice is often sticky, which leads to "clumping" and easier eating with chopsticks. As such, Asian meals generally do not require any use of Western eating utensils, with the exception, perhaps, of the addition of a spoon, which is popular in Korea. On the other hand, food prepared using Western methods tend to require Western eating utensils, as they are often prepared in larger pieces and need to be cut with a fork and a knife. Even similar size foods can vary in their ability to be handled with a particular eating utensil—rice prepared using Western cultural methods tend be "fluffy", for example, and is particularly difficult to eat with chopsticks. The availability of multifunctional eating utensils is limited, and none of those that are available provide the benefits that result from the dining kit of the present invention. For example, two of the most recognized forms of such utensils are the "spork" (spoon/fork) and "knork" (knife/fork), neither of which provide chopstick functionality. Examples of patents directed to multi-functional eating utensils include U.S. Pat. Nos. 5,056,173; 5,791,053; and 6,067,717.

Since people commonly have different preferences for eating utensils, and since such preferences and needs should be respected in all sectors of society, including private and commercial sectors, there is a great need for an international dining kit that provides for, and respects, these personal preferences and needs. One of skill will appreciate that such a kit can be beneficial and useful in about any location having an international presence. These locations, for example, can include any place where people can gather to dine, such as the private home; schools; restaurants; fast food franchises; and travel and recreation providers, which include, but are not limited to, the airline industry, trains, cruise ships, and the like. Those skilled in the art will readily recognize that multifunctional eating utensils are currently unavailable in a form that is useful and practical, such that they are affordable and readily accessible, particularly considering the need for ease of packaging, storage, and use, as well as the need for utensils that are disposable and/or biodegradable.

SUMMARY

The embodiments taught herein relate generally to an international dining kit comprising a pair of multifunctional chopstick components. The dining kit generally comprises a first chopstick component having a fork portion and a first chopstick portion; and a second chopstick component having a spoon portion and a second chopstick portion. And, in some embodiments, at least one of the components is disposable and/or biodegradable.

In some embodiments, the fork portion is releasably connected to the first chopstick portion and the spoon portion is releasably connected to the second chopstick portion. In some embodiments, the first chopstick component is releasably connected to the second chopstick component. In most embodiments, the components are releasably connected to one another using a means that is selected for ease of packaging and ease of use.

In some embodiments, the components of the dining kit can be further modified to provide additional functionality. For example, the first chopstick component, the second chopstick component, or both, can be hollow to function as a straw for drinking. In fact, the dining kit can further comprise a straw component for drinking as well.

In some embodiments, the dining kit can provide a personal hygiene functionality. In these embodiments, the dining kit can further comprise a dental cleaning component selected from a group consisting of a toothpick, dental floss, toothbrush, or a combination thereof. In these embodiments, the dental cleaning component can comprise a toothpick.

In some embodiments, the international dining kit can further comprise a knife component having a blade portion and a handle portion. In these embodiments, the first chopstick component, the second chopstick component, and the knife component can be releasably connected to one another by at least two releasable connections, and can be connected using a means that is selected for ease of packaging and ease of use.

In embodiments further comprising a dental cleaning component, the components can be releasably connected to one another by at least three releasable connections, and the components can be releasably connected to one another using a means that is selected for ease of packaging and ease of use.

DETAILED DESCRIPTION

The embodiments of the present invention are generally directed toward an international dining kit having a pair of multifunctional chopstick components. The components include a first chopstick component having a fork portion and a first chopstick portion; and a second chopstick component having a spoon portion and a second chopstick portion.

In some embodiments, the term "chopsticks" can refer to two rods having a top and bottom area that is smaller than one square centimeter. Chopsticks vary with respect to length, tapering, and construction material, and the end with a smaller diameter usually comes in contact with the food. Very long chopsticks, sometimes upwards of a meter in length, but usually about thirty or forty centimeters, tend to be used for cooking, especially for deep frying foods. Shorter chopsticks are generally used as eating utensils but are nevertheless used in the kitchen for cooking. The tapered end used to pick up food can be a blunt or a pointed end. Blunt ends provide more surface area for holding food and for shoveling rice. Pointed ends provide easier manipulation of food, such as picking out bones from whole cooked fish.

Figure 1:
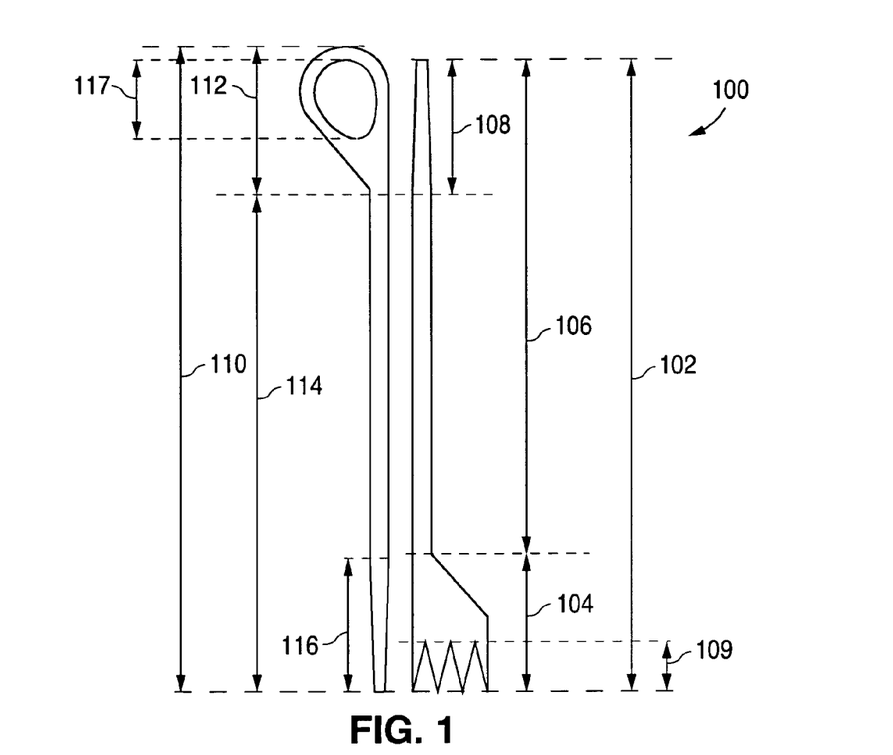
FIG. 1 illustrates a dining kit containing a first chopstick component having a fork portion and a first chopstick portion; and a second chopstick component having a spoon portion and a second chopstick portion, according to some embodiments of the present invention.

FIG. 1 illustrates a dining kit containing a first chopstick component having a fork portion and a first chopstick portion; and a second chopstick component having a spoon portion and a second chopstick portion, according to some embodiments of the present invention. Dining kit 100 contains a first chopstick component 102 having a fork portion 104 and a first chopstick portion 106; and a second chopstick component 110 having a spoon portion 112 and a second chopstick portion 114. The first chopstick component 102 can also have a tapered end 108 and fork tongs 109 for engaging with food while eating. The second chopstick component 110 can also have a tapered end 116 and a spoon dish 117 for engaging with food while eating.

The fork portion 104 and the spoon portion 112 can be any variation of shape and size that would still provide the intended use of the present invention. In one example, the fork portion 104 can be a "spork" in some embodiments, which is known to one of skill as a cross between a spoon and a fork. In another example, the fork portion 104 can have fork tongs 109 that form an intersecting wedge between the individual tongs, as shown in FIG. 1, or the individual tongs can be parallel to one another, such as is commonly seen with ordinary table forks. In another example, the fork portion 104 can any number of fork tongs 109, ranging from a single tong to about 6 tongs, from about 2 tongs to about 5 tongs, from 3 tongs to 5 tongs, 4 tongs as shown in FIG. 1, or any range therein. In another example, the spoon portion 112, can be oval as in FIG. 1, round, square, rectangular, or any other shape that will provide the intended utility of a spoon. In another example, the spoon portion 112 can have a spoon dish 117 that is oval as in FIG. 1, round, square, rectangular or any other shape that will provide at least the utility of carrying an amount of a fluid. In another example, the spoon portion 112, and the spoon dish 117 can be paired with any combination of shapes, such as a round spoon portion 112 and an oval spoon dish 117, or an oval spoon portion 112 and a round spoon dish 117, etc.

The fork portion 104 can be in line with, or at an angle with, the central axis of the first chopstick portion 106. Likewise, the spoon portion 112 can be in line with, or at an angle with, the central axis of the second chopstick portion 114. In some embodiments, the angle can range from about 0° to about 60°, from about 0° to about 50°, from about 0° to about 45°, from about 0° to about 40°, from about 0° to about 35°, from about 0° to about 30°, from about 0° to about 25°, from about 0° to about 20°, from about 0° to about 15°, from about 0° to about 10°, from about 0° to about 5°, from about 2° to about 30°, from about 4° to about 25°, from about 6° to about 15°, or any range therein. The angle can be measured at any point in the fork portion 104, such as the fork tongs 109, relative to the first chopstick portion 106. Likewise, the angle can be measured anywhere in the spoon portion 112, such as the spoon dish 117, relative to the second chopstick portion 114.

In some embodiments, the fork portion 104 can have fork tongs that range in length from about 0.2 cm to about 6.0 cm, from about 0.5 cm to about 3.0 cm, from about 0.75 cm to about 2.0 cm, from about 1.0 cm to about 1.5 cm, or any range therein. In some embodiments, the spoon portion 112 can have a spoon dish 117 with a capacity of about 0.2 ml to about 20 ml, from about 0.5 ml to about 10 ml, from about 0.75 ml to about 7.5 ml, from about 1.0 ml to about 5.0 ml, from about 1.0 ml to about 4.0 ml, from about 1.5 ml to about 3 ml, about 1.75 ml to about 2.75 ml, from about 2.0 ml to about 2.5 ml, or any range therein.

In some embodiments, the first chopstick portion 106 and second chopstick portion 114 can each range in length from about 12 cm to about 40 cm, from about 12 cm to about 35 cm, from about 12 cm to about 30 cm, from about 14 cm to about 30 cm, from about 14 cm to about 25 cm, from about 14 cm to about 20 cm, from about 16 cm to about 20 cm, or any range therein.

The first chopstick portion 106 and second chopstick portion 114 can have ends that are straight or tapered. In some embodiments, the tapered ends 114 and 116 can blunt or pointed. A cross-section of the tapered ends 114 and 116 will show any of a variety of geometries known to one of skill in the manufacture of chopsticks. In some embodiments, the tapered ends 114 and 116 can be round, triangular, square, pentagonal, hexagonal, heptagonal, octagonal, and the like.

In some embodiments, the tapered ends 114 and 116 can be smooth or textured, where the texturing can include circumferential rings, knurling, etching, barbs, or any other texturing known to one of skill to assist in holding food with the tapered ends 114 and 116. In some embodiments, the tapered ends 114 and 116 can have a preselected surface tension, such that the food does not tend to stick onto the surfaces. In these embodiments, the preselected surface tension can be created through selection of polymers, polymer mixtures, polymer coatings, surface treatments such as oxidation, halogenation, grafting, ion bombardment, and the like, to create the desired chemical functionalities at the surface of the tapered end. In these embodiments, a slippery surface can be modified with texturing to allow for the necessary gripping of food during eating.

The components in the dining kit can be manufactured using any material known by one of skill in the art of producing eating utensils. In some embodiments, the components can be made from a metal, and in some of these embodiments, the metal can be selected from a group consisting of silver, steel, pewter, electroplated nickel silver, or stainless steel. In some embodiments, the components can be made from plastic. In some embodiments, the components can be made from bamboo, plastic, wood, bone, metal, jade, or ivory.

Components made of bamboo or wood, are cheap to make, low in temperature conduction, and provide a good grip for holding food due to their matte surfaces. However, these materials can warp, deteriorate with continued use, and harbor bacteria if not properly cleaned. Disposable unlacquered wood, for example, is often used to produce restaurant grade chopsticks, and these chopsticks can come as a partially cut structure that must be broken into two chopsticks by the user. Plastic components are also cheap to make, low in temperature conduction, do not harbor bacteria, or deteriorate significantly with continued use. Plastic components, however, cannot be used for cooking, since high temperatures may damage them and produce toxic compounds. Metal components, on the other hand, can be more expensive to make, but they are durable, and easy to clean. Unfortunately, metal is slippery, does not hold food as well as other materials, and its higher heat conduction makes it uncomfortable to use in cooking. Materials such as ivory, jade, gold, and silver can also be used but are typically chosen for extravagance.

In many embodiments, the dining kits of the present invention, or components therein, can be entirely manufacture, or at least partially manufactured, using molding procedures known to one of skill in the art. These molding procedures can include, but are not limited to, extrusion molding, injection molding, and foam molding.

In extrusion molding, solid polymeric materials can be added to a continuous melt that is forced through a die and cooled to a solid form. The solid form may require additional processing to obtain the final product in a desired form. The solid polymeric materials can be in the form of particles that can vary in mean diameter from about 1 mm to about 1 cm, from about 1 m to about 10 mm, from about 1 nm to about 1 mm, from about 1 mm to about 100 nm, or any range therein.

In injection molding, solid polymeric materials are added to a heated cylinder, softened and forced into a mold under pressure to create a solid form. The solid form may require additional processing to obtain the final product in a desired form. The solid polymeric materials can be in the form of particles that can vary in mean diameter from about 1 mm to about 1 cm, from about 1 nm to about 10 mm, from about 1 mm to about 1 mm, from about 1 nm to about 100 mm, or any range therein. Injection molding of a material comprising 70% general purpose polystyrene (GPPS) and 30% high-impact polystyrene (HIPS), is used in one embodiment of the present invention. Generally speaking, heated plastic is forced under pressure into a hardened steel or aluminum mold cavity, clamped together, and solidified into the shape of the mold creating the part. The quality of the molded part depends on the quality of the mold, so care should be taken during the molding process and design of the part. It is also essential that the molten resin chosen for injection be at just the right pressure and temperature so that it flows easily to all parts of the mold. In addition, the parts of the mold must also come together extremely precisely, otherwise small leakages of molten plastic can form, a phenomenon known as flash which requires extra labor to trim by hand. When filling a new or unfamiliar mould for the first time, where shot size for that particular mold is unknown, the manufacturer should reduce the shot size and nozzle pressure so that the mould fills 90-95%, thus creating a "short shot". Then, using that now-known shot volume, pressure can be raised without fear of damaging the mould. Sometimes factors such as venting, temperature, and resin moisture content, can effect the formation of flash as well.

In foam molding, blowing agents are used to expand and mold solid polymeric materials into a desired form, and the solid polymeric materials can be expanded to a volume ranging from about two to about 50 times their original volume. The polymeric material can be pre-expanded using steam and air and then formed in a mold with additional steam; or mixed with a gas to form a polymer/gas mixture that is forced into a mold of lower pressure. The solid form may require additional processing to obtain the final product in a desired form. The solid polymeric materials can be in the form of particles that can vary in mean diameter from about 1 nm to about 1 cm, from about 1 nm to about 10 mm, from about 1 nm to about 1 mm, from about 1 nm to about 100 nm, or any range therein.

In some embodiments, the dining kit, or components therein, can be formed by injection molding or extrusion of a layer followed by cutting a pattern of a dining kit, or a component therein into the layer. In one example, the pattern can be cut with a laser. In some embodiments, the dining kit, or components therein, can be formed using a layered manufacturing process, which includes the use of a rasterizing laser to selectively polymerize a polymer solution into the desired shapes of the dining kit or components. The desired shapes are translated into a mathematical algorithm that guides the formation of the dining kit or components one layer at a time, for example, from a vat of liquid polymer using methods known to one of skill.

Any polymer, copolymer, or mixture of polymers known to one of skill to provide the requisite physical performance requirements can be used in the present invention. In some embodiments, the polymers that can be used include natural or synthetic polymers; homopolymers and copolymers, such as, for example, copolymers that are random, alternating, block, graft, and/or crosslinked; or any combination and/or blend thereof. The copolymers include, but are not limited to, polymers with two or more different types of repeating units such as, for example, terpolymers. The polymer mixtures can be a combination of 2, 3, 4, or more polymers, where the composition determines the performance characteristics of the end-product. The mixture can also be supplement with fillers, dyes, and the like. In a binary mixture of polymers, for example, the combination of polymers can provide a tuned property of the end product, which may include, but is not limited to, flexibility, rigidity, brittleness, chemical resistance, biodegradability, and the like.

In some embodiments, the polymer or combination of polymers are thermopolymers. In some embodiments, the thermoplastic material that can be used can include polystyrene, acrylonitrile butadiene styrene (ABS), nylon, polypropylene, polyethylene, and polyvinyl chloride or PVC. The material used in some embodiments of the present invention includes about 70% general purpose polystyrene (GPPS) and about 30% high-impact polystyrene (HIPS). In some embodiments, a first component can range from 0-100%, 1-95%, 2-90%, 4-85%, 5-75%, 10-50%, or any range therein, and the remaining polymers can be added to compose the remainder of the mixture, and a filler or dye can be added to compose a portion of the mixture as well.

In some embodiments, the polymers used in the compositions of the present invention can have a crystallinity at 40° C. that is less than 50 weight percent (wt %), less than less than 30 wt %, less than 20 wt %, or a combination thereof. While not intending to be bound by any theory or mechanism of action, the term "crystallinity" can refer to regions in which polymer chains align with one another, usually parallel, to form crystalline lattices in an effort to obtain the most favorable thermodynamics.

There are a variety of methods used to determine percent crystallinity of a polymer, and each of these methods, although well-known to those skilled in the art, is usually expected to produce a somewhat different crystallinity measurement than may be obtained using a different measurement method for a given polymeric material. While not intending to be bound by any theory or mechanism of action, percent crystallinity can be determined using calorimetry such as, for example thermogravimetric analysis/differential scanning calorimetry; spectroscopy such as, for example, infrared spectroscopy and nuclear magnetic resonance spectroscopy; x-ray diffraction techniques, such as wide-angle x-ray diffraction; gravimetric determinations, including density determinations, specific volume measurements, and the like.

In some embodiments, the polymers include, but are not limited to, poly(acrylates) such as poly(butyl methacrylate), poly(ethyl methacrylate), poly(hydroxyethyl methacrylate), poly(ethyl methacrylate-co-butyl methacrylate), and copolymers of ethylene-methyl methacrylate; poly (2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; and any derivatives, analogs, homologues, congeners, salts, copolymers and combinations thereof.

In some embodiments, the polymers include, but are not limited to, fluorinated polymers or copolymers such as poly(vinylidene fluoride), poly(vinylidene fluoride-co-hexafluoropropene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters; poly(olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

In some embodiments, the polymers include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

The dining kit can be designed such that the components can be physically altered by the user. In some embodiments, the fork portion is releasably connected to the first chopstick portion and the spoon portion is releasably connected to the second chopstick portion. The releasable connection allows the fork and spoon portions to be selectively detached from the chopstick portions.

The dining kit can come as a partially, or fully, connected unit, such that the user will need to separate at least some of the components from one another prior to use. In some embodiments, the first chopstick component is releasably connected to the second chopstick component. In most embodiments, the components are releasably connected to one another using a means that is selected for ease of packaging and ease of use.

The term "releasably connected," "releasable connection," and the like, can generally be used interchangeably throughout this application, and refers to any means of connecting portions to each other, components to each other, or portions to components, such that the connections are relatively easily disconnected by a user through the application of a reasonable amount of force, wherein a "reasonable amount of force" can be an amount of force that can be applied by a small person, child, or elderly person to separate the components from each other, or portions from the components. In some embodiments, the releasable connection includes a breakable connection made of bamboo, plastic, wood, or metal. These releasable connections can be formed, for example, using any method known to one of skill, such as through a plastic mold, a punch and die, a thermal weld, a solvent weld, or by creating a weakened section in a material. A weakened section can be created, for example, through a narrowing or selective positioning of a fracture point, such as a wood grain or other known material weakness. In some embodiments, the releasable connection can include a mechanical connection such as a coupling means. Examples of coupling means include spring clips, tongue-and-groove, plug-and-socket, threaded couples, friction couples, welded couples, and the like, which can be released by the user.

Figure 2:
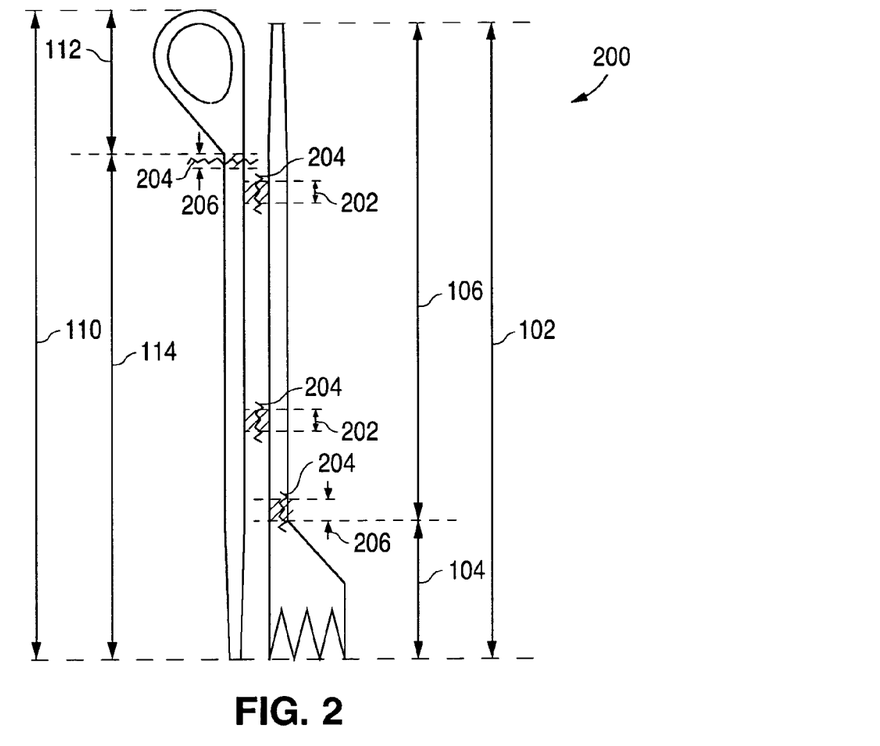
FIG. 2 illustrates a dining kit containing releasable connections between components and between portions within components, according to some embodiments of the present invention.

FIG. 2 illustrates a dining kit containing releasable connections between components and between portions within components, according to some embodiments of the present invention. Dining kit 200 contains releasable connections 202 between components 102 and 110 and releasable connections 206 between portions 112 and 114, and 104 and 106, within components 102 and 110. A break 204 is created in the releasable connections 202 and 206 by applying an amount of pressure to sufficient fracture the releasable connection. Breaking 204 the releasable connection 202 between components 102 and 110 is necessary to use the dining kit 200, and breaking the releasable connection 206 between portions 112 and 114, and 104 and 106, allow for use of the chopstick portions 106 and 114 without the fork and spoon portions 104 and 112.

The dining kit can be further modified to provide additional functions. In some embodiments, the international dining kit includes a knife component having a blade portion and a handle portion. In some embodiments, the first chopstick component, the second chopstick component, or both, are hollow to function as a straw for drinking. In some embodiments, a separate straw component can be further provided as an additional means for drinking.

Figure 3:
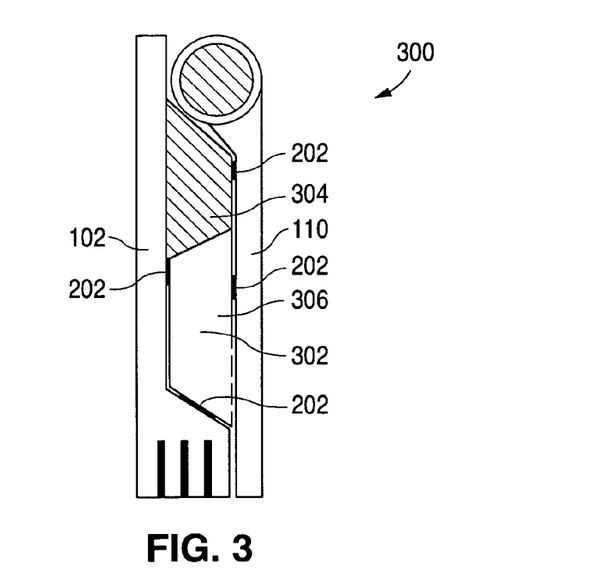
FIG. 3 illustrates a dining kit modified to contain a knife, according to some embodiments of the present invention.

FIG. 3 illustrates a dining kit modified to contain a knife, according to some embodiments of the present invention. Dining kit 300 has a first chopstick component 102, second chopstick component 110, and a knife 302. The first chopstick component 102 and second chopstick component 110 are releasably connected 202 to the knife 302 having a blade portion 304 and a handle portion 306.

In many embodiments, a personal hygiene functionality can be provided by other available dining kits. In these embodiments, the dining kits of the present invention can include a dental cleaning component selected from a group consisting of a toothpick, dental floss, toothbrush, or a combination thereof. In some embodiments, the dental cleaning component comprises a toothpick.

Figure 4:
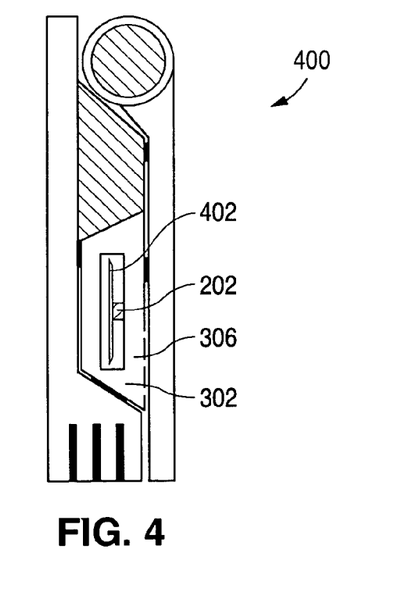
FIG. 4 illustrates a dining kit modified to contain a dental cleaning component, according to some embodiments of the present invention.

FIG. 4 illustrates a dining kit modified to contain a dental cleaning component, according to some embodiments of the present invention. Dining kit 400 comprises dining kit 300 and a toothpick 402 releasably connected 202 to the handle portion 306 of the knife 302. As would be recognized by one of skill currently available dining kits are not manufactured to contain a dental cleaning component as part of the kit. In some embodiments, the dental cleaning component can be a specialized interproximal dental cleaning device presented in U.S. Pat. No. 3,101,727, which is hereby incorporated herein by reference in its entirety.

Figure 5A:
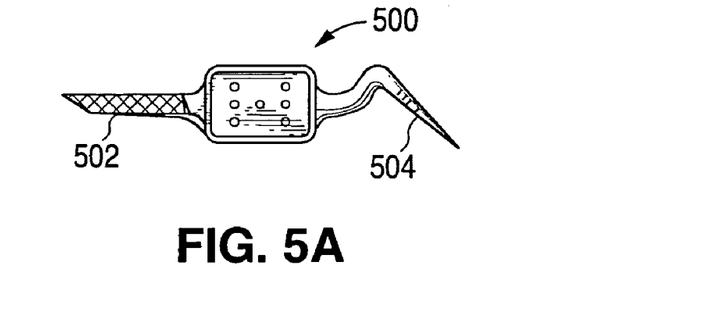
FIG. 5A-5C illustrate the interproximal dental cleaning device, according to some embodiments of the present invention.
Figure 5B:
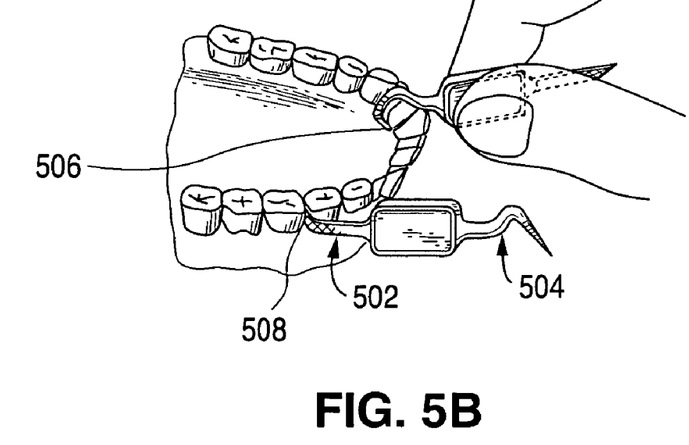
Figure 5C:
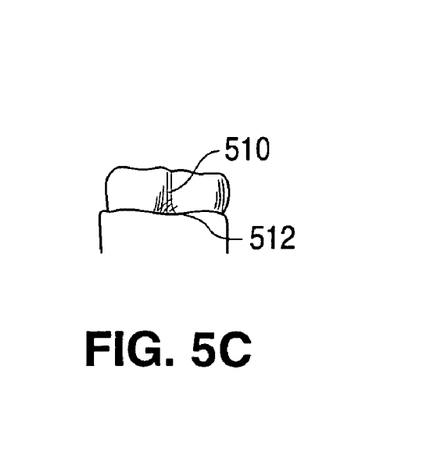

FIGS. 5A-5C illustrate the interproximal dental cleaning device, according to some embodiments of the present invention. Known as a Pick-A-Dent®, and described in U.S. Pat. No. 3,101,727 above, this dental cleaning component 500 can be formed with the dining kits of the present invention to clean food from the interproximal regions between teeth. As shown in FIG. 5A, the dental cleaning component 500 has a blade portion 502 and contra-angle pick portion 504. As shown in FIG. 5B, the blade portion 502 and contra-angle pick portion provides functional capabilities that include, but are not limited to, cleaning of lingual-facing interproximal areas 506, and buccal interproximal areas 508 that a standard toothpick may not be able reach without risk of tissue damage. As depicted in FIG. 5C, failure to remove food from the interproximal regions between teeth will result in oral hygiene damage including, but not limited to, caries 510 between teeth and gingivitis 512 that can result in symptoms such as halatosis and irrecoverable tissue loss to tooth enamel, dentin, nerve tissue, vascular tissue, and gingiva.

In embodiments that include a first chopstick component, a second chopstick component and a third component, such as a knife component, the components are sometimes releasably connected to one another by at least two releasable connections, and these connections can be placed and provided for ease of packaging.

The following example is presented to describe a method of making the dining utensil of the present invention.

EXAMPLE

The articles of the present invention can be produced using an injection molding process. The material used in this embodiment is 70% general purpose polystyrene (GPPS) and 30% high-impact polystyrene (HIPS), and the material can be in the form of resin pellets. A desired dye color can be added. The raw material is in a dry location or by drying it in an oven before use to avoid surface defects, short shots, stress lines, flow lines, and silvering.

These resin pellets are poured into a feed hopper, which is a large open bottomed container used to feed the resin pellets down to the screw. The screw is turned by hydraulic or electric motor to feed the pellets up the screw's threads. The depths of the threads decrease towards the end of the screw nearest the mold. As the screw rotates, the pellets are moved forward in the screw and undergo extreme pressure and friction to generate most of the heat needed to melt the pellets. Heaters on either side of the screw assist in the heating and temperature control around the pellets during the melting. The screw-travel-limit switches set the distance the screw can move.

The hydraulic system pumps oil from the oil tank to firmly close the male and female mold parts. The resin is now a liquid, and the liquid resin is injected into the mold. Since the molds are clamped shut by the hydraulics, the heated plastic is forced under the pressure of the injection screw to take the shape of the mold. Water-cooling channels assist in cooling the mold, and the heated plastic solidifies into the part. Improper cooling can result in a distorted or burned molding. The cycle is completed when the mold opens and the part is ejected with ejector pins within the mold.

The end product is broken off the injection gates and packed in a pre-printed polybag.

Those skilled in the art will recognize, or be able to ascertain using no more than routine experimentation, that there are many equivalents to the specific embodiments described herein that have been described and enabled to the extent that one of skill in the art can practice the invention well-beyond the scope of the specific embodiments taught herein. Such equivalents are intended to be encompassed by the following claims. In addition, there are numerous lists and Markush groups taught and claimed herein. One of skill will appreciate that each such list and group contains various species and can be modified by the removal, or addition, of one or more of species, since every list and group taught and claimed herein may not be applicable to every embodiment feasible in the practice of the invention. All publications, patents, and patent applications mentioned in this application are herein incorporated by reference into the specification to the same extent as if each was specifically indicated to be herein incorporated by reference in its entirety.

I claim:

1. An international dining kit comprising:
a pair of multifunctional chopstick components comprising a first chopstick component having a fork member and a first chopstick member with a substantially planar first surface; and a second chopstick component having a spoon member and a second chopstick member with a substantially planar second surface; and
a knife component having a blade member and a handle member, wherein the first chopstick component, the second chopstick component, and the knife component are directly and breakably connected to one another by at least two weakened sections so that the first surface, the second surface, and at least one of the blade portion or the handle portion are substantially coplanar;
wherein the spoon member is adjacent to an end of the first chopstick member that is opposite the fork member, and the fork member is adjacent to an end of the second chopstick member that is opposite the spoon member when the first chopstick component, the second chopstick component, and the knife component are breakable connected to one another; and
wherein the fork member is at an angle relative to a central axis of the first chopstick member, the spoon member is at an angle relative to a central axis of the second chopstick member, and the knife component is between the first chopstick member, the second chopstick member, the fork member and the spoon member, the knife component having a central longitudinal axis that is parallel to the central axes of the first and second chopstick members, wherein the fork member and the spoon member extend across the central longitudinal axis of the knife component so that the fork member and the spoon member flank the knife component along its central longitudinal axis.

2. The dining kit of claim 1, wherein the fork member is breakably connected to the knife component and the knife component is breakably connected to the second chopstick member.

3. The dining kit of claim 1, wherein an end of the knife component terminates at an angle that is similar to the angle of the fork member relative to the central axis of the first chopstick member.

4. The dining kit of claim 1, wherein an end of the knife component terminates at an angle that is similar to the angle of the spoon member relative to the central axis of the second chopstick member.

* * * * *